(12) United States Patent
Liu et al.

(10) Patent No.: US 7,173,242 B2
(45) Date of Patent: Feb. 6, 2007

(54) METHOD FOR DETERMINING WHETHER A ROCK IS CAPABLE OF FUNCTIONING AS AN OIL RESERVOIR

(75) Inventors: Keyu Liu, Bateman (AU); Peter John Eadington, Como (AU); Joseph Stanley Kurusingal, Cherrybrook (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 298 days.

(21) Appl. No.: 10/470,136

(22) PCT Filed: Jan. 21, 2002

(86) PCT No.: PCT/AU02/00060

§ 371 (c)(1),
(2), (4) Date: Dec. 22, 2003

(87) PCT Pub. No.: WO02/059581

PCT Pub. Date: Aug. 1, 2002

(65) Prior Publication Data

US 2004/0099804 A1    May 27, 2004

(30) Foreign Application Priority Data

Jan. 23, 2001  (AU) .................... PR5145
Jul. 20, 2001  (AU) .................... PR6507

(51) Int. Cl.
  *G01N 21/64*  (2006.01)
(52) U.S. Cl. ..................................... 250/301
(58) Field of Classification Search ................ 250/301
  See application file for complete search history.

(56) References Cited

U.S. PATENT DOCUMENTS 2,227,438 A * 1/1941 Campbell ............... 250/255

| | | |
|---|---|---|
| 4,609,821 A | 9/1986 | Summers |
| 4,814,614 A | 3/1989 | Tsui |
| 4,856,351 A | 8/1989 | Smith et al. |
| 5,049,738 A | 9/1991 | Gergely et al. |
| 5,241,859 A | 9/1993 | Smith |
| 5,543,616 A | 8/1996 | Eadington et al. |
| 6,271,518 B1 | 8/2001 | Boehm et al. |

* cited by examiner

*Primary Examiner*—Constantine Hannaher
(74) *Attorney, Agent, or Firm*—Merchant & Gould P.C.

(57) ABSTRACT

A method is defined for determining whether a rock is capable of functioning as an oil reservoir has had or presently contains oil. The method includes the steps of: -cleaning a sample of the rock in a manner such that at least some of any adsorbed oil on the rock will remain and any oil inclusions within the rock remain intact; -irradiating the cleaned sample with fluorescence inducing electromagnetic (typically UV) radiation and measuring emitted (typically UV and visible) radiation from the sample; and-comparing the emitted radiation measurement against a similarly determined measurement from a rock sample of a known oil-producing reservoir, to determine whether or not the rock has had or presently contains oil. In a variation of the above method, the sample of the rock is cleaned step-wise in a manner that removes other than adsorbed oil on the rock, with a final cleaning step including contacting the sample with a solvent into which some adsorbed oil may be extracted. The solvent extract can then be analysed for oil (typically by irradiating the solvent with fluorescence inducing electromagnetic (typically UV) radiation) and the analysed oil then compared against a similarly derived and analysed oil from a rock sample of a known oil reservoir to determine whether or not the rock has had or presently contains oil. Typically the rock is granular and typically the cleaning step involves disaggregating the rock into single grains, prior to cleaning.

15 Claims, 9 Drawing Sheets

METHOD FOR DETERMINING WHETHER A ROCK IS CAPABLE OF FUNCTIONING AS AN OIL RESERVOIR

FIELD OF THE INVENTION

The present invention relates to a method for the location of oil producing reservoirs, by determining the presence of a reservoir that has had or may presently contain oil.

BACKGROUND TO THE INVENTION

When rock formations in the subsurface are saturated with or exposed to oil, either in rocks capable of trapping oil, or in oil migration pathways, residual oil may remain. Reservoir rock that once contained high oil saturation will generally hereinafter be referred to as a "palaeo oil zone". The traces of remaining oil are referred to as oil shows or residual oil.

Existing techniques that detect palaeo oil zones may also detect current oil zones. Also, detection of oil accumulation and migration in the geological past is critical for the evaluation of oil exploration wells. During and after drilling a well, there are a number of ways of detecting whether rocks are currently oil saturated, or have been oil saturated. These include detecting the concentration and composition of gas in drilling mud using gas chromatography; visual inspection to detect fluorescence in core or cuttings; repeat formation tests (RFT) to make pressure measurements, drill stem tests (DST) to obtain samples of pore fluid, and geophysical measurements (logging) to detect changes in resistivity in the rock formation.

Some of these methods are too expensive to implement on every exploration well. Also, these methods cannot always adequately detect palaeo oil zones due to drainage of most of the oil, such that the residual oil is less than the sensitivity of the methods or due to obscuring of residual oil by contamination introduced during the drilling or testing processes. Oil-based drilling mud and some mud additives also fluoresce under ultraviolet light and the residual oil viewed may in fact be contamination.

Oil inclusions in rock grains have been used to indicate the presence of palaeo oil, and an abundance of oil inclusions can be used to indicate palaeo oil saturation semi-quantitatively. Fluid inclusion technology is used to evaluate palaeo oil accumulation and migration in exploration and appraisal.

One method to evaluate palaeo oil saturation using oil inclusions is outlined in U.S. Pat. No. 5,543,616, where grains containing oil inclusions are counted. Another method is fluid inclusion stratigraphy (FIS) (as set forth in U.S. Pat. No. 4,856,351 and U.S. Pat. No. 5,241,859). FIS is an analytical technique that involves automated mass spectrometer analysis of volatile compounds released by crushing samples of sedimentary rock after an aqueous based cleaning procedure. When grains containing oil inclusions are crushed the inclusion oil will be detected as volatile compounds. However, not all rocks that have been in contact with oil contain oil inclusions because the formation of oil inclusions requires healed micro-fractures or overgrowths on grains at the time of oil charge and migration.

Oil may also be retained in a rock because of incomplete drainage, for example due to capillary or wettability effects. Previous attempts to detect oil shows using fluorescence have detected residual oil surrounding grains or have measured the oil dissolved in solvent extracts from rock samples of cuttings and core obtained during drilling (eg. U.S. Pat. Nos. 4,609,821, 4,814,614; 5,049,738).

SUMMARY OF THE INVENTION

In a first aspect, the present invention provides a method for determining whether a rock that is capable of functioning as an oil reservoir has had or presently contains oil, including the steps of:

(i) cleaning a sample of the rock in a manner that removes other than oil adsorbed on the rock and such that at least some of the oil adsorbed on the rock remains and any oil inclusions within the rock remain intact;

(ii) irradiating the cleaned sample with fluorescence inducing electromagnetic radiation and measuring emitted radiation from the sample; and (iii) comparing the emitted radiation measurement against a similarly determined measurement from a rock sample of a known oil reservoir, to determine whether or not the rock has had or presently contains oil.

In a second aspect, the present invention provides a method for determining whether a rock that is capable of functioning as an oil reservoir has had or presently contains oil, including the steps of:

(i) step-wise cleaning a sample of the rock in a manner that removes other than adsorbed oil on the rock, with a final cleaning step including contacting the sample with a solvent into which some adsorbed oil may be extracted; and either:

(iia) irradiating the cleaned rock sample with fluorescence inducing electromagnetic radiation and measuring emitted radiation from the sample; or (iib) analysing oil extracted into the solvent of the final cleaning step; and (iii) in the case of step (iia) comparing the emitted radiation measurement against a similarly determined measurement from a rock sample of a known oil reservoir; or in the case of step (iib) comparing the analysed oil against a similarly derived and analysed oil from a rock sample of a known oil reservoir;

to determine whether or not the rock has had or presently contains oil.

The present inventors noted that oil may be adsorbed at rock surfaces by chemical and physical attraction and may be trapped as inclusions within the rock (eg. within grains). Further, the present inventors surprisingly discovered that by directly measuring the oil adsorbed at the grain surface and any inclusion oil, or measuring adsorbed oil in a solvent extract thereof, rather than measuring oil dissolved within cleaning solvent used in the cleaning step, and then comparing that against measurements from a known reservoir, less contamination prone and more accurate predictions about oil occurrence and/or the rock's oil history can be made.

PREFERRED FEATURES OF THE INVENTION

Preferably in step (iib) the oil analysis involves irradiating the solvent with fluorescence inducing electromagnetic radiation and measuring emitted radiation from the solvent.

An advantage of using a fluorescence spectrophotometer in this regard is its ease of use in the field, and its more robust configuration. However, once the oil is in a solvent, other analysis techniques can be employed, such as chemical analysis (eg. using gas chromatography or mass spectrometer analysis) etc.

Typically the method is employed with rock that is granular, the rock being disaggregated into single grains prior to cleaning step (i).

Preferably the sample or solvent is irradiated with ultraviolet (UV) radiation and characterising fluorescence spectra of the adsorbed oil and any oil inclusions, or solvent extracted oil, is measured.

To excite the oil, it is preferred that the sample or solvent is irradiated with UV radiation including wavelengths of about 253 nm (sample) or 260 nm (solvent), respectively. Preferably the characterising fluorescence spectrum is measured in the range of 300 to 600 nm, using a fluorescence spectrophotometer. Preferably a mean intensity of emitted radiation normalised to that at 300 nm is computed for wavelengths of 375 to 475 nm, and is then compared against that of a known rock sample.

Preferably step (i) involves cleaning the sample in a manner that removes liquid oil and weakly adsorbed oil Preferably, when the rock is granular, the sample is disaggregated into single grains and step (i) then includes the steps of:

(a) sieving the sample; and (b) subjecting the sieved sample to ultrasound and solvent washing/digestion.

Preferably the step (b) solvent washing/digestion includes washing the grains with water and dichloromethane, and digestion with hydrogen peroxide solution and acid solution, to ensure maximal removal of readily soluble hydrocarbons.

Preferably a final step of solvent washing is employed in step (i) of the first aspect. Preferably the solvent used for solvent washing is dichloromethane (although other solvents can be used).

Preferably the final step solvent is discarded in the case of step (iia) of the second aspect or can be used as the solvent for step (iib) of the second aspect.

Trace 1: Typical fluorescence for non-functionalized 3-ringed aromatic compounds;

Trace 2: Typical fluorescence for non-functionalized 4-ringed aromatic compounds;

Trace 3: Fluorescence of asphaltene type compounds extracted from a sample of North Sea oil;

Trace 4: Fluorescence of NSO type compounds extracted from a sample of North Sea oil;

Traces 5 and 6: Fluorescence of the extracted polar compounds from two different production wells Australia's NW Shelf.

Figure 3:
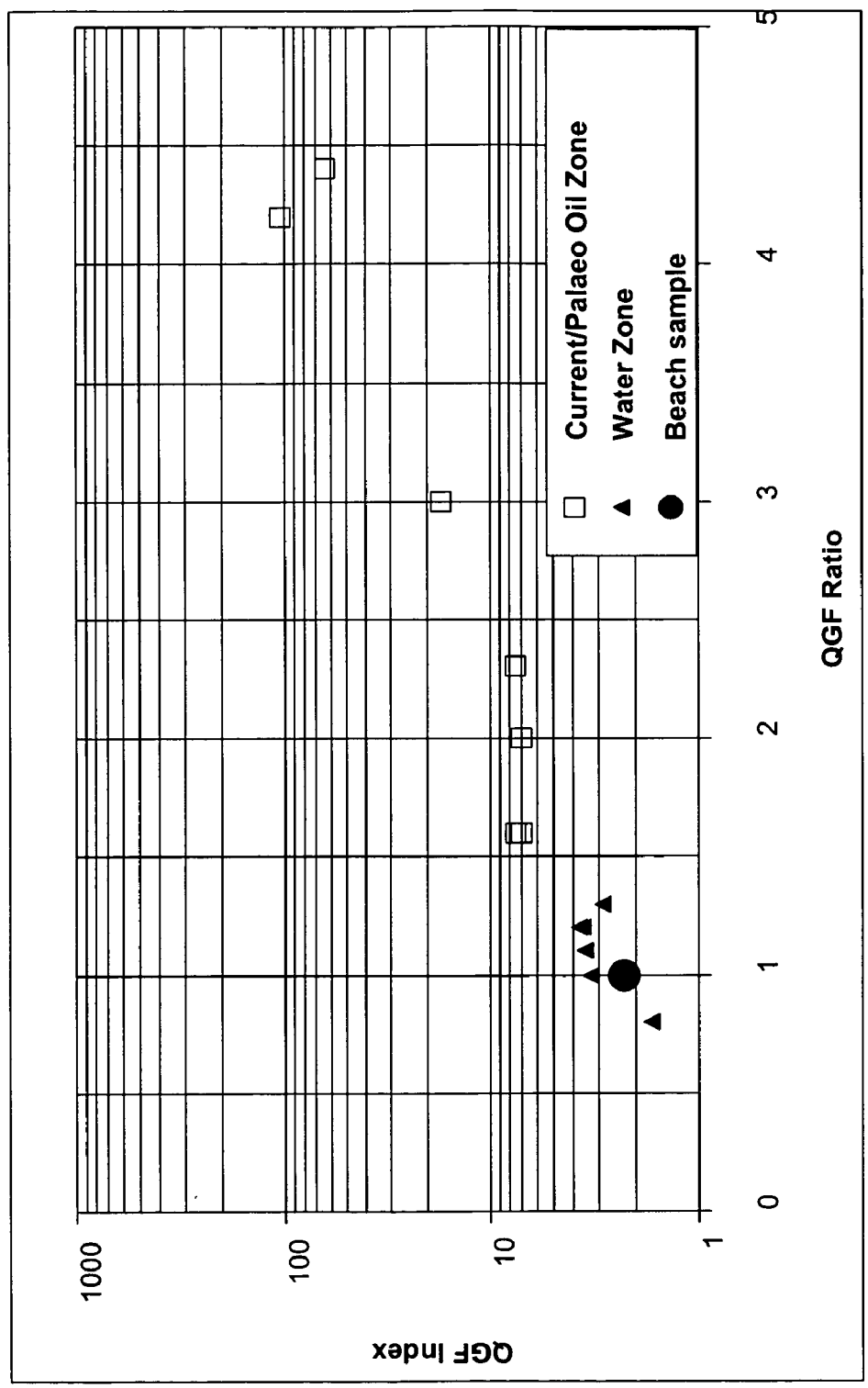

FIG. 3 QGF Index and QGF Ratios cross plot for water zone, palaeo/current oil zone samples from seven wells from three different basins in the NW Shelf showing the clearly defined empirical thresholds for water and current/palaeo oil zone samples.

Figure 4:
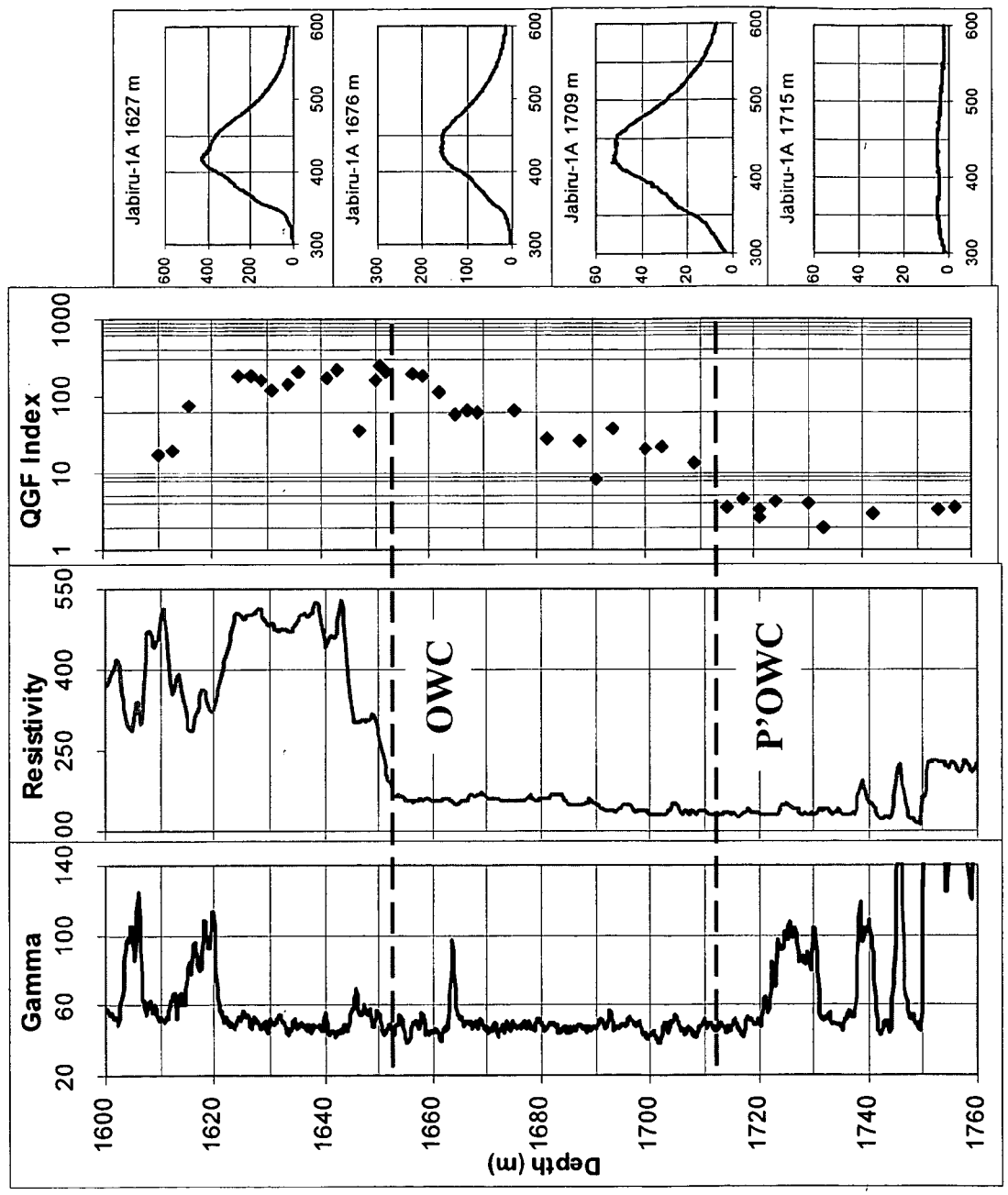

FIG. 4 QGF Index profile through a reservoir in the Timor Sea. OWC refers to current oil-water contact determined by repeated formation test (RFT), geophysical log analysis and laboratory fluid saturation analyses. P'OWC refers to the palaeo oil and water contact defined by the GOI technique. Sample depths for QGF spectra are in the heading to each graph.

Figure 5:
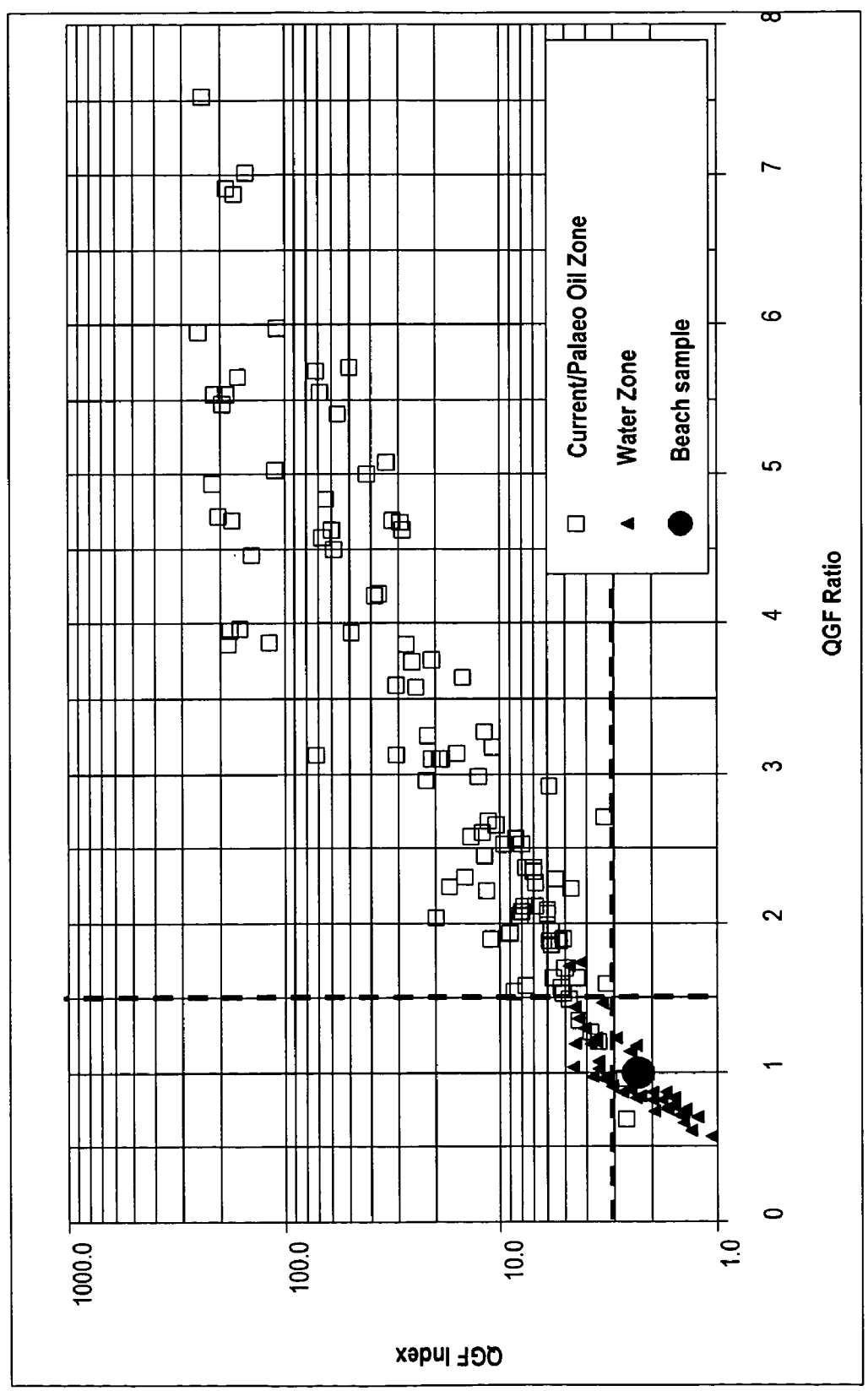

FIG. 5 QGF Index and Ratios cross plot for 150 samples from seven exploration and production wells and one modern beach sand.

Figure 6:
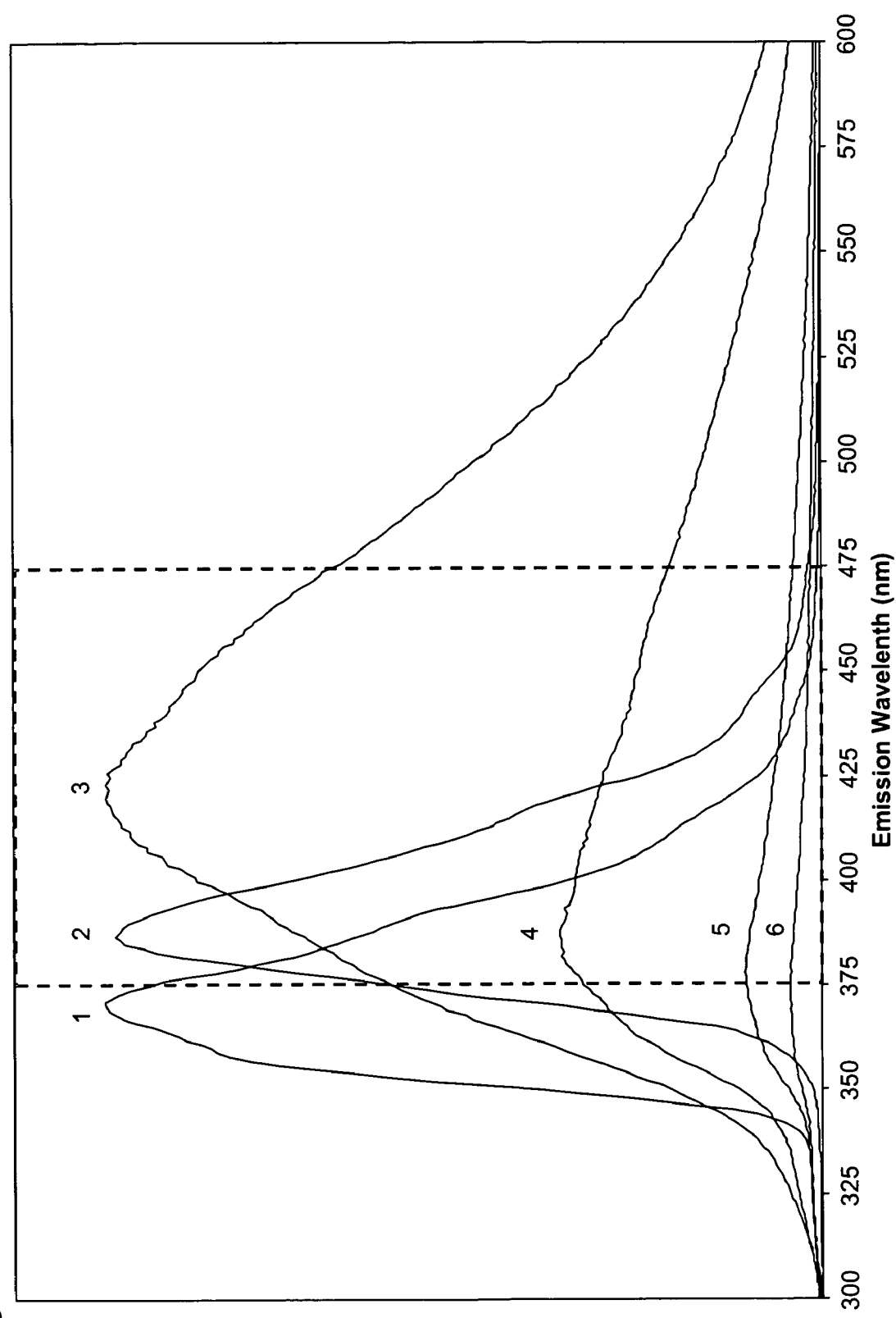

FIG. 6 Fluorescence spectra of multi-ringed aromatic and polar compounds found in oils. The QGF-E intensity is the intensity at the wavelength of maximum fluorescence.

Trace 1: Fluorescence for 3-ringed aromatic hydrocarbon (retene);

Trace 2: Fluorescence for 4-ringed aromatic hydrocarbon (pyrene);

Trace 3: Fluorescence of asphaltenes separated from a sample of North Sea oil (NSO-1: Norwegian Petroleum Directorate);

Trace 4: Fluorescence of polar compounds separated from a sample of North Sea oil (NSO-1: Norwegian Petroleum Directorate);

Trace 5: Fluorescence of the extracted polar compounds from Jabiru 1A crude oil;

Trace 6: Fluorescence of the extracted polar compounds from Skua crude oil.

Figure 7:
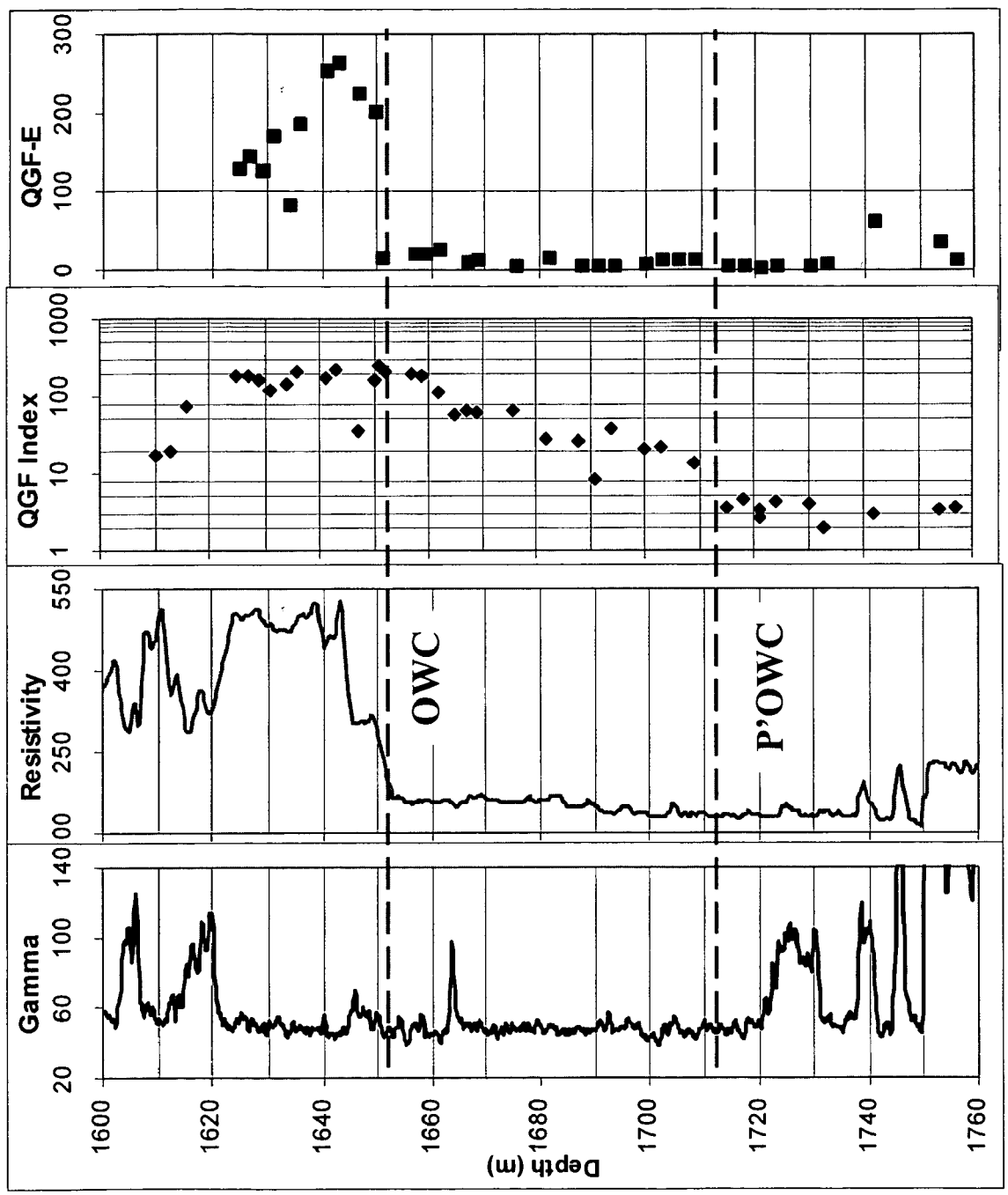

FIG. 7 QGF and QGF-E intensities for samples from Jabiru-1A.

Figure 8:
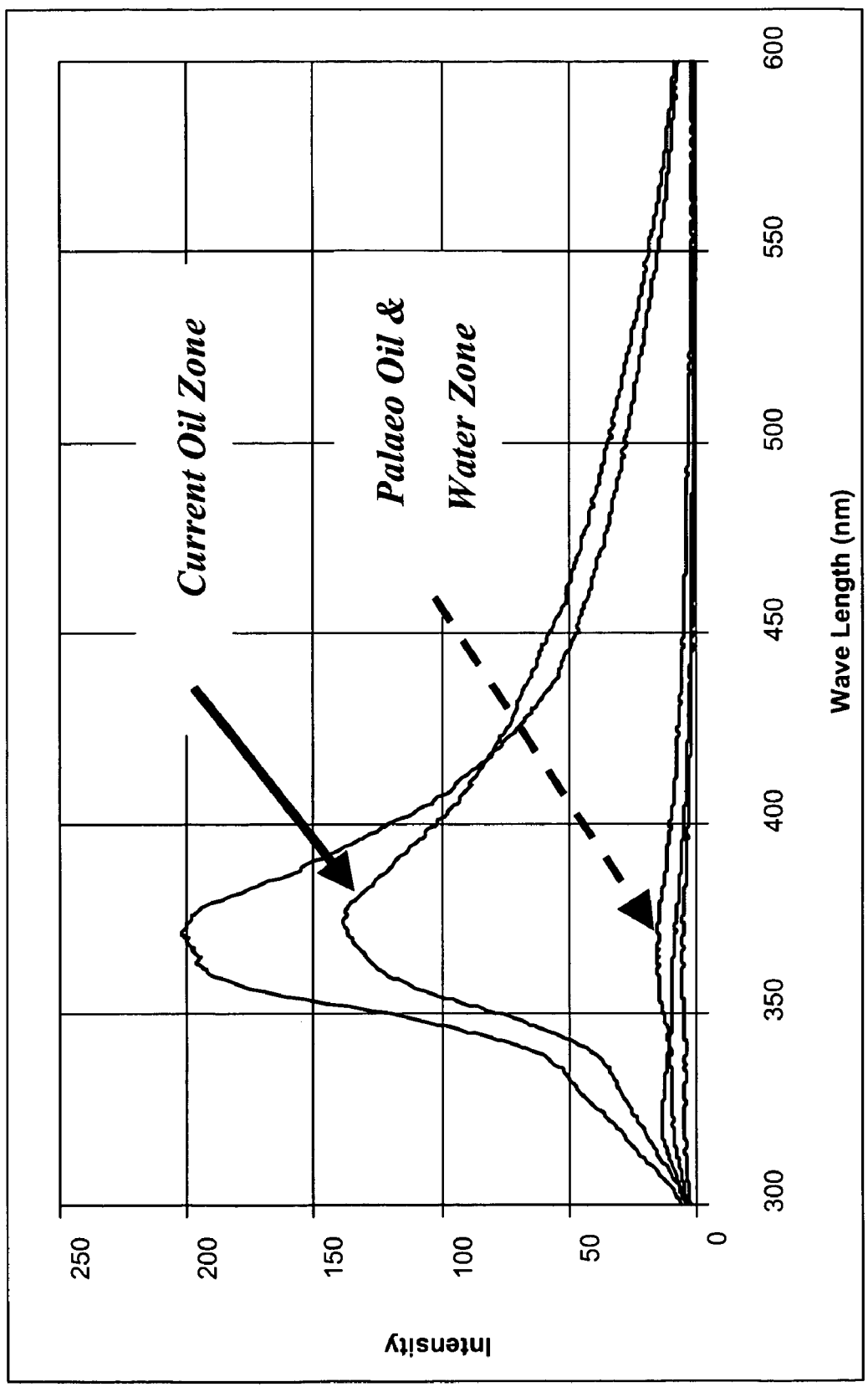

FIG. 8 QGF-E fluorescence spectra for samples from Jabiru-1A.

Figure 9:
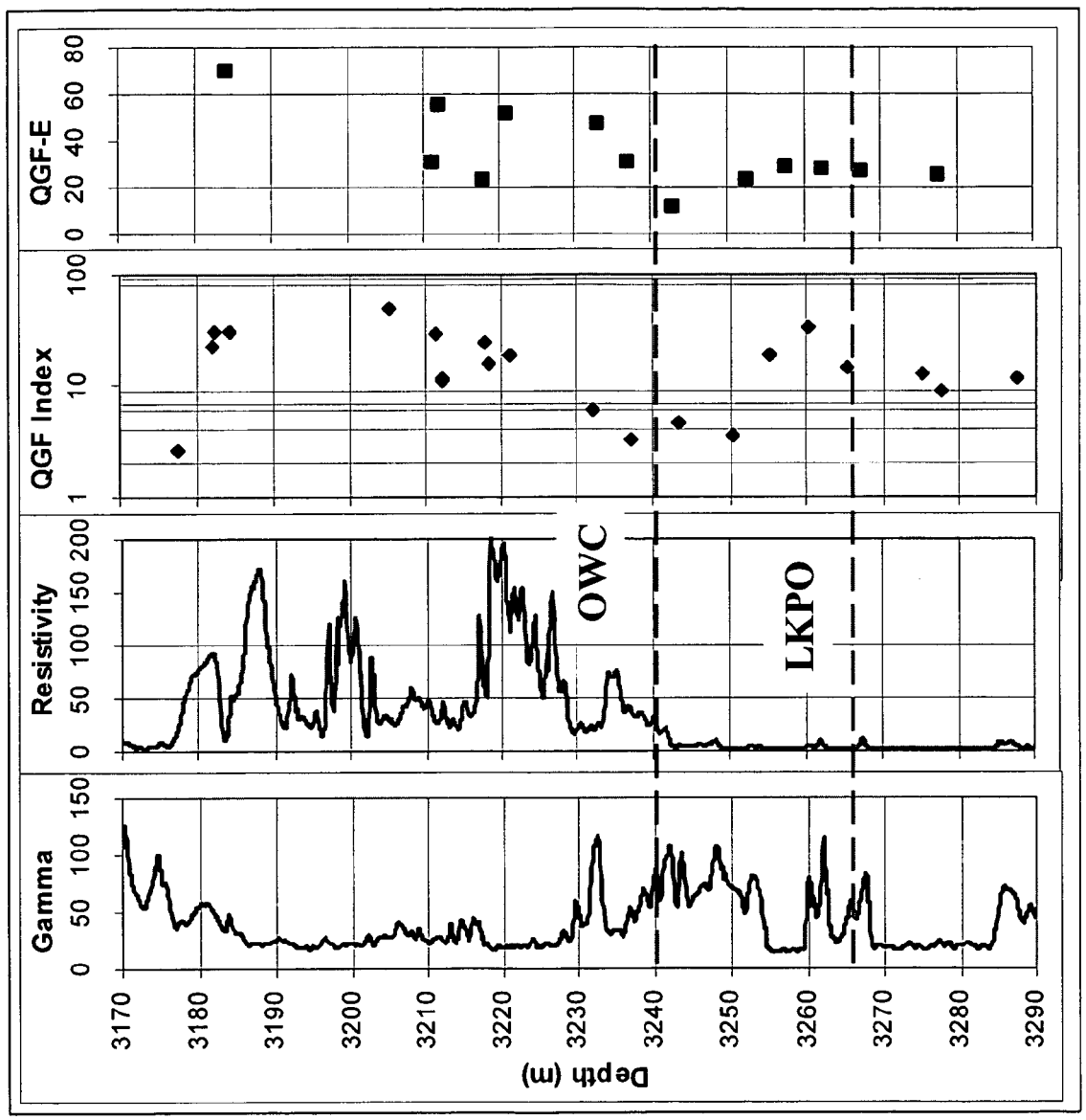

FIG. 9 Graph of QGF Index and ZGF-E versus depth for the Corallina-1 oil well.

MODES FOR CARRYING OUT THE INVENTION

The preferred methods now described will generally be referred to as quantitative grain fluorescence (QGF) methods. A variation on QGF, known as QGF-E is also described. The preferred methods are by no means to be seen to be limiting of the invention and are provided by way of example only.

Overview of the QGF Method

QGF was developed by the inventors to more reliably detect current day-oil zones and palaeo oil zones. The present inventors had noted that oil adsorption at grain surfaces could occur by chemical and physical attraction, and that oil inclusions could be trapped in framework grains during oil charge and migration processes.

Whilst the chemical and physical attraction typically occurs at rock grain surfaces, and whilst the inclusions are typically intragranular, the present invention is not limited to use on granular rocks such as sandstone. For example, the methods of the present invention can be applied to amorphous rocks such as opal and coal, and also rocks with very small grains such as jade.

Chemisorption was noted to occur when a chemical bond was formed between an oil molecule and a mineral surface. Physical adsorption was noted to occur when hydrocarbons were held by intermolecular forces, most notably by electrostatic attraction of polar molecules by surface charge. Oil droplets could be captured as inclusions in microfractures and grain boundaries by thermal healing and in diagenetic overgrowth.

A first aspect of the present invention involves the discovery that certain compounds in oil that are strongly adsorbed on mineral surfaces and which remain after a preferred cleaning process will fluoresce, together with any inclusion oils sealed in the rocks (eg. within grains), when illuminated by ultraviolet light, and this fluorescence can be meaningfully measured and comparatively analysed. This method is referred to as QGF.

A second aspect of the present invention involves the discovery that at least a portion of the compounds, which remain after the preferred cleaning process, can be solvent extracted and then measured. In particular, these compounds will fluoresce in the solvent extract when illuminated by ultraviolet light, and again this fluorescence can be meaningfully measured and comparatively analysed. This method is referred to as QGF-E.

In QGF, a fluorescence spectrophotometer was used to illuminate with UV light a bulk sample of grains from a reservoir rock, such as sandstone, and to measure the total fluorescent light emitted from the sample, referred to as the Quantitative Grain Fluorescence. In QGF-E, a fluorescence spectrophotometer was used to illuminate with UV light a solvent containing oil extracted from grains from the reservoir rock, and to measure the total fluorescent light emitted from the sample, referred to as the Quantitative Grain Fluorescence-Extract.

Fluorescent light emission was detected at one or several wavelengths, or wavelength bands, which were selected by measuring the UV fluorescence spectrum of a representative sample.

The threshold values of QGF and spectral features for oil zones and palaeo oil zones were determined by analysis of samples of reservoir rock from oil producing reservoirs. A baseline QGF and spectral features were determined by analysis of samples from water producing intervals located below a current oil zone and below any suspected residual zones. The instrumental response to grains with minimal hydrocarbon content or influence was determined by measuring the QGF and spectral features of a sample of sand grains from a modern beach deposit that had no oil inclusions and had been repeatedly cleaned to minimise the adsorbed oil on the surface.

The QGF methods used samples of rock cuttings and core routinely produced during the drilling process and it was therefore noted that the methods could be used at the well site for rapid detection of current day oil zones, and palaeo oil zones.

Sample preparation was used to remove any liquid or weakly adsorbed surface hydrocarbons so that only the fluorescence emitted by strongly bound, residual hydrocarbons (or of at least some of such hydrocarbons in a solvent extract), and emitted by inclusion oil sealed in the grains, was measured. Sample preparation comprised disaggregating the sample into single grains, wet sieving to remove the clay fraction, and ultrasonic cleaning of the grain surfaces. The grains were then washed with dichloromethane, digested in 10% hydrogen peroxide and in 3.6% hydrochloric acid. In QGF a further wash of surface hydrocarbons, again using dichloromethane, was employed. However, for QGF-E, this further wash comprised the solvent extraction step.

In QGF fluorescence spectral intensity was then measured on these "cleaned" grains. In QGF-E the further solvent wash was recovered and fluorescence spectral intensity was measured on this solvent extract.

QGF and QGF-E data for samples from an oil well were displayed as spectra at wavelengths of 300 to 600 nm. Depth logs of the QGF intensity (average fluorescence intensity between 375 and 475 nm) QGF Index (average fluorescence intensity between 375 and 475 nm normalised against spectral intensity at 300 nm) or QGF-E intensity (the maximum intensity between 300 and 600 nm) were also displayed. Other single valued parameters that summarised the response observed in the spectra were also able to be plotted in a depth log.

Data manipulations to enhance the difference between oil zone or palaeo oil zone and water zone samples included taking a ratio between the fluorescence intensity at peak height and at the spectral baseline, or by taking the ratio of fluorescence intensity at two spectral peaks, such as the QGF ratio (ratio of average fluorescence intensities between 375 and 475 nm and the fluorescence intensity at 350 nm) and/or alternative spectral intensity parameters.

Samples from current day-oil zones were recognised by the presence of spectral peaks compared with baseline spectra and by elevated values of QGF intensity, QGF Index or QGF-E intensity, and QGF ratio. Samples from palaeo oil zones were recognized by the presence of spectral peaks compared with baseline spectra and by elevated values of QGF Index and QGF ratio. Baseline response for a particular well was established from water zone samples.

The presence of spectral peaks and elevated values of QGF Index or QGF-E intensity and QGF ratio were confirmed as palaeo oil zones by calibration using well site test data where available (eg oil recovery, direct core fluorescence) and by comparison with typical QGF Index or QGF-E intensity and QGF ratio and spectral shapes that were established from measurements on samples from known oil producing zones.

Palaeo oil zones were noted to indicate proximity to oil accumulations. Detecting current oil zones or palaeo oil zones before the drill rig was moved prompted additional testing to be made at the well site that might not have been made without such data. The inventors noted that should a palaeo oil zone be detected sufficiently quickly a sidetrack well may be drilled to locate a current day oil accumulation in proximity to the first drill site.

The QGF and QGF-E techniques used simple sample preparation, and spectral measurements were able to be made in minutes (a desirable feature for use on exploration rigs). Thus, the techniques were employable at a well site for rapid detection of current day oil zones, palaeo oil zones and oil migration pathways, thus indicating proximity to producible oil.

The methods were noted to differ from existing methods that used fluorescence spectrometry to detect palaeo oil zones, in that the QGF technique measured hydrocarbons strongly adsorbed on grain surfaces that remained after an appropriate cleaning step (eg. washing with solvent and oxidative and acidic digestion) and measured any oil sealed in inclusions, whereas the QGF-E technique measured hydrocarbons in a solvent extract carried out after an appropriate cleaning step (eg. washing with solvent and oxidative and acidic digestion) to remove liquid and weakly adsorbed or degraded hydrocarbons.

The QGF method thus detected residual oil that was strongly bound to grain surfaces and any oil that was trapped in inclusions, while the QGF-E method detected residual oil that was strongly bound to grain surfaces. Existing methods were, on the contrary, noted to measure hydrocarbons in a first solvent wash. In the prior art these strongly bound residual hydrocarbons were previously regarded as negligible and too low in concentration to measure by fluorescence techniques. The QGF and QGF-E methods thus provided a cost-effective technique to detect current day oil zones and palaeo oil zones.

EXAMPLES

Example 1

The Quantitative Grain Fluorescence (QGF) Method

The QGF method was developed to provide the oil industry with a cost-effective, rapid and simple screening technique, primarily to detect palaeo oil zones within reservoir rocks (being the zones that may indicate commercial oil quantity elsewhere in the reservoir). The method measured the intensity of fluorescence emitted from rock grains under UV excitation after washing with solvent and digestion with hydrogen peroxide to remove any undrained oil or weakly adsorbed compounds. The rock samples were taken at a depth interval within an oil well using the procedures described below. Interpretation of the QGF intensity profile or QGF Index profile, and presence or absence of spectral peaks, determined whether the samples were from an oil zone, a palaeo oil zone or oil migration pathway in the interval of rock formation investigated.

In the QGF technique palaeo oil zones were identified as zones with fluorescence intensity from rock grains, cleaned by the preferred process, that were elevated above baseline values that occurred in rocks that have always been water saturated. Spectra of oil zone samples had observed spectral peaks whereas spectra of samples from water zones were relatively flat.

Fluorescence Spectra of Hydrocarbons at Grain Surfaces

Figure 1:
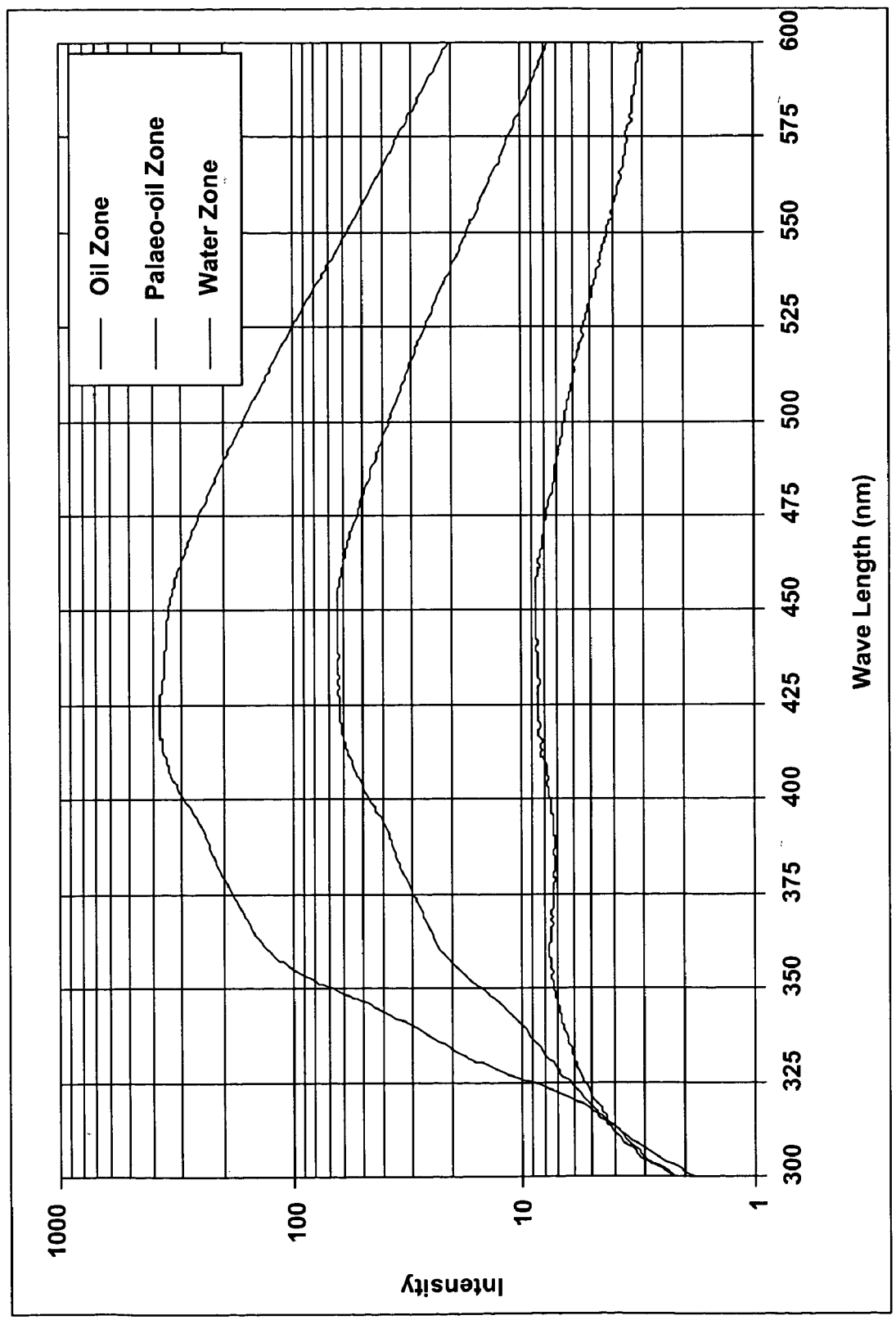
FIG. 1 Fluorescence spectra of samples of sand (quartz) grains from current oil zone, palaeo oil zone and water zone from a reservoir sequence in the Timor Sea, NW Shelf, Australia.

FIG. 1 presents fluorescence spectra from quartz grains that were washed with solvent and digested in hydrogen peroxide and hydrochloric acid. The spectra presented were for samples that were measured with a 253 nm excitation wavelength, from a current oil zone, a palaeo oil zone and a water zone.

Experiments were carried out to test if UV fluorescence from strongly adsorbed hydrocarbons and any oil inclusions was capable of differentiating samples from known oil, palaeo oil and water zones. The fluorescence intensity was measured at selected wavelengths. The measurements were of a series of samples that had been previously analysed using the applicant's GOI method (U.S. Pat. No. 5,543, 616.). The UV fluorescence intensity of samples from the current oil zone and palaeo oil zone was observed to be several times higher than that from the water zone. FIG. 1 showed that the emission spectra intensity from hydrocarbons tightly bound to quartz grains and inclusion oils could be used to quantitatively discriminate a current oil zone and a palaeo-oil zone from a water zone.

Measuring the Quantitative Grain Fluorescence

The steps in the application of the QGF method included a sample selection protocol, a sample preparation procedure to remove weakly bound hydrocarbons, illumination of the sample with an optimal excitation wavelength, recording of the fluorescence emission spectrum, and extracting selected parameters from the data. The QGF spectrum was measured in all samples taken from the oil well being investigated.

Samples were prepared by washing with solvent and digestion with hydrogen peroxide to remove liquid oil and weakly adsorbed hydrocarbons from the surfaces of whole grains from reservoir rock, and digestion with hydrochloric acid to remove potentially fluorescing grains such as carbonate minerals. Quantitative Grain Fluorescence was measured by illuminating a known amount of clean rock grains (often quartz or feldspar) with UV light and measuring the intensity of the total fluorescence emitted by hydrocarbons tightly bound to the grains and any oil trapped in inclusions. The QGF data were used to deduce spatial patterns of oil saturation in reservoir rock. The QGF method was developed using a modified Cary Eclipse model of a Varian UV fluorescence spectrophotometer.

Sample Selection and Preparation

A continuous QGF profile was obtained for the interval of reservoir rock being investigated. A sample was taken at every cuttings interval (typically 3 m or 5 m intervals) and core was sampled at a comparable frequency. Samples of water zone outside the interval of immediate interest were also obtained to establish baseline QGF values. Water zone samples were noted to typically occur at the base of reservoir rocks, below oil zones or palaeo oil zones.

The sample preparation procedure (Table 1) comprised disaggregation of samples of core and cuttings into single grains, and chemical cleaning of the grain surfaces.

1. Separation of Single Rock Grains

Core and cuttings samples were disaggregated into their component framework grains by gentle agitation. The grains were either dry or wet-sieved to select the >63 μm and <1 mm size fraction depending on the size range of the samples. The sieving removed the bulk of shale in the samples. Where a high proportion of shale or coal fragments diluted the quartz and feldspar grains then a grain concentrate was made by techniques such as magnetic separation (Franz Isodynamic Separator), heavy liquid or panning device.

2. Surface Cleaning

The rock grains were first rinsed with water for 10 minutes in an ultrasound bath to separate particles (eg. clay) and remove any liquid oil loosely adhering at the grain surface. Samples were oven dried at 60° C. then washed with dichloromethane (DCM) in an ultrasound bath for 10 minutes to remove liquid oil and weakly bound surface hydrocarbons or organic contaminants. The sample was then digested in 10% $H_2O_2$ at room temperature for 1 hour with periodic agitation to degrade and further remove weakly bound residual organic compounds. The grains were digested in 3.6% hydrochloric acid (HCl) for 20 minutes with periodic agitation to remove any carbonate minerals that might produce mineral fluorescence. Finally, the grains were washed again with dichloromethane (DCM) in an ultrasound bath for 10 minutes (see Table 1 below) to remove some residual hydrocarbons or organics. In the QGF-E technique (described below) this second DCM wash comprised the solvent extraction step. The remaining grains were observed to comprise predominantly quartz and feldspar.

TABLE 1

Procedure to clean quartz grains for QGF analysis.

| Disaggregation | Mineral separation | Water | DCM (Dichloro methane) | $H_2O_2$ (10%) | HCl (3.6%) | DCM (Dichloro methane) |
|---|---|---|---|---|---|---|
| Core or Cuttings Crushed and sieved to obtain grains in the <1 mm >0.18 mm fraction | Electro-magnetic separation of quartz grains if required | 10 minute ultrasound bath | 10 minute ultrasound bath | 1 hour digestion at room temperature | 20 minute digestion | Ultrasound bath for 10 minutes |

In removing liquid oil and weakly bound hydrocarbons this procedure minimised the signal resulting from variations in the saturation of residual oil and from contaminants introduced by drilling processes and sample handling.

Instrument Setup and Measurement Procedure

A fluorescence spectrophotometer was used to carry out the QGF measurement. A narrow band interference filter was added to the excitation monochromator of the instrument to reduce the stray light level of the monochromator.

An excitation wavelength of 253 nm was found to be optimal for the analysis. This excitation wavelength was selected to excite fluorescence in a wide range of compounds and to produce maximum fluorescence intensity. Spectral measurements were made after loading the samples in a multi-chamber sample holder containing samples in 96 wells. Each cell had a volume of approximately 330 $mm^3$. Laboratory measurements indicated that the UV light penetrated at least the top 3 mm of the rock grains. The rock grains were compacted and levelled prior to loading in the spectrophotometer. Multiple cells were also loaded and analysed at the same time. The measurement of a sample was replicated by measuring multiple sub-samples from each sample, and an average spectrum was obtained by taking at each wavelength the average of the intensities of the replicate measurements. All subsequent analysis was of the intensities of this average spectrum.

Diminution of fluorescence intensity due to absorption and scattering of light arising from variation in grain properties such as grain size, shape, packing, and colour was partly compensated for by measuring replicate spectra on sub samples. Other procedures to measure and compensate for diminution of intensity due to grains included the addition of a compound with well-characterised fluorescence as an internal standard, and the measurement of an absorption spectrum on the grains and the monitoring of the fluorescence intensity at 300 nm, which was noted to be outside the wavelength band of most interest.

QGF Spectrum

The shape of the QGF spectrum was displayed to observe spectral features. The spectral shape was used to discriminate between oil zone, palaeo oil zone and water zone samples.

QGF Intensity

The QGF ratio was calculated as the average fluorescence intensity in the range 375–475 nm measured at 1 nm intervals. This was a single valued parameter suitable for plotting against depth to discriminate between oil or palaeo oil zones and a water zone.

QGF Index

The QGF Index was calculated as the average fluorescence intensity in the range 375–475 nm measured at 1 nm intervals normalised against the spectral intensity at 300 nm. This was found to give improved discrimination between the spectra of samples from oil/palaeo oil zone and water zone (FIGS. 1 and 3) compared with QGF intensity. Applications of QGF are presented below using QGF Index.

Figure 2:
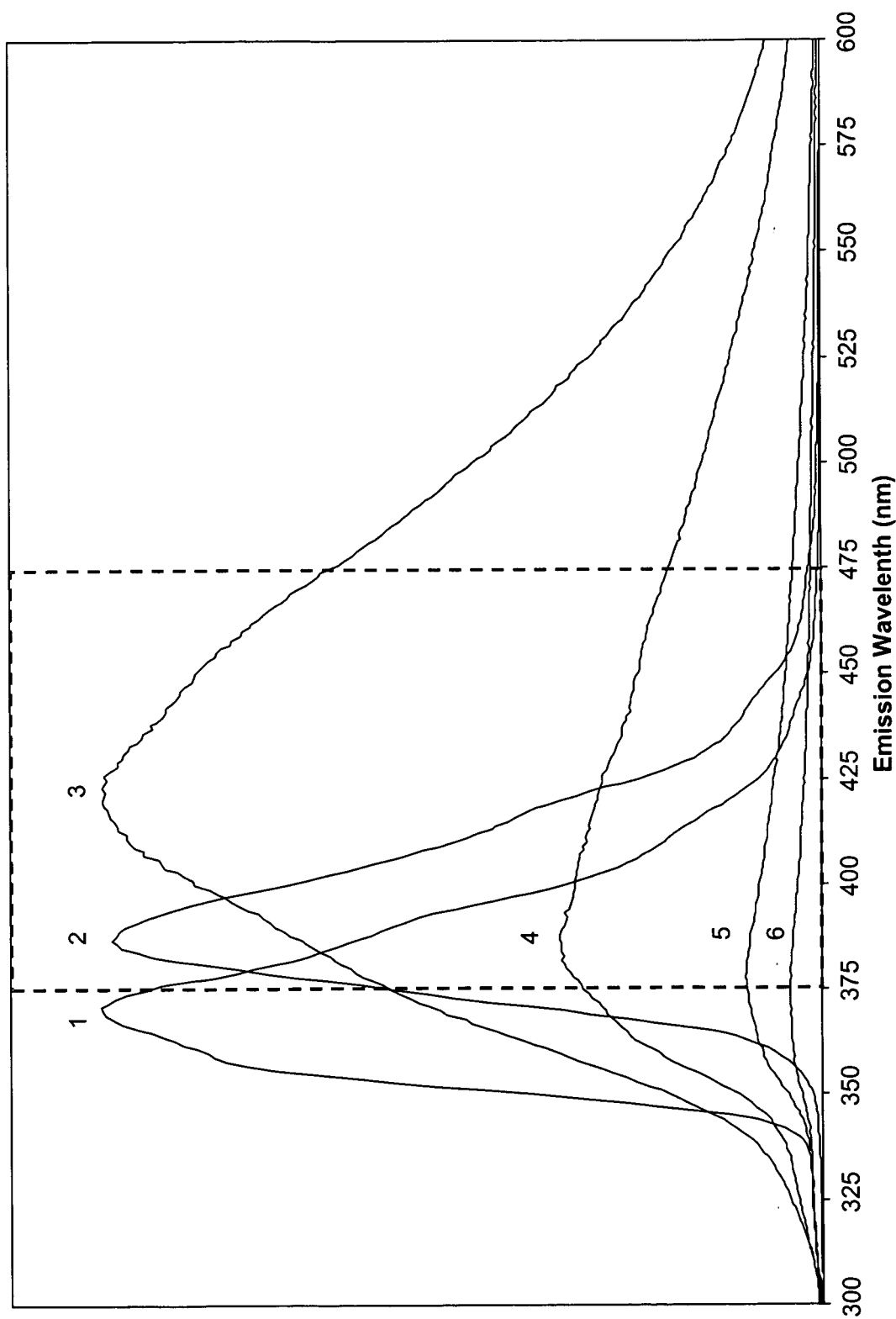
FIG. 2 Typical Fluorescence spectra of a selection of multi-ringed aromatic and polar compounds typically found in oils. The QGF Intensity was taken as the average fluorescent intensity recorded between 375–475 nm.

The strongly bound hydrocarbons and inclusion oil, which were detected in QGF, were observed to primarily include the high molecular weight aromatic and polar compounds adsorbed at grain surfaces and trapped in inclusions. Four types of polar compounds displayed maxima in fluorescence emission in the 375–475 nm wavelength interval (FIG. 2). These materials were noted to be fractions of natural crude oil produced by liquid chromatography.

Samples with a low QGF response including water zone and beach sand samples that had not been exposed to oil sometimes had a small maximum in fluorescence intensity at wavelengths near 350 nm (see eg. FIG. 4 spectrum for 1715 m sample). Because of the possible influence of sample attributes including the brightness of the surfaces of the rock grains being analysed on this part of the spectrum, a bandwidth that excluded wavelengths near 350 nm was selected to minimise this effect.

QGF Ratio

A QGF ratio was established as the ratio between the average fluorescence emission intensities from 375 to 475 nm to the intensity at 350 nm. The 375 to 475 nm wavelength coincided with the maximum peak of QGF measured from reservoir samples (FIG. 1) and was used for QGF Index determination. The 350 nm wavelength was outside the main area of interest in the spectrum.

The QGF Index reflected total fluorescence emission from sand grains, whereas the QGF ratio accounted for the shape of the fluorescence spectra. The combination of both parameters leads to an effective interpretation of fluorescence emission and was used for comparison and correlation between oil wells.

Interpretation of Oil Saturation

The QGF Index for samples within the depth intervals of interest was plotted as a depth profile beside one or more geophysical logs (e.g. gamma ray log, density, or neutron porosity logs, resistivity log), which would serve as a correlation tool and reservoir quality reference. QGF Index and QGF Ratio cross plot can also be used to differentiate samples from current/palaeo oil zones and water zones with references of known oil and water zone samples. Complete spectra for some or all the samples were also displayed.

The interpretation involved establishing baseline values of spectral shape, QGF Index, and QGF ratio for the reservoir interval being evaluated. Then palaeo oil zones were identified where QGF Index was anomalously high, had observed spectral peaks and was differentiated from baseline values by exceeding QGF Index and Ratio thresholds. Thresholds were not global and were established in the region being investigated by measuring samples from known oil producing zones, palaeo oil zones, water zones and modern beach sand as reference material. Also, QGF spectra were observed to be relatively flat for water zone samples and to have spectral peaks typically between 400 and 500 nm in oil zone and palaeo oil zone samples.

TABLE 3

Summary of QGF data for 150 samples from seven wells and one beach sand sample, showing average QGF Index and Ratios for multiple samples from known current oil zone, palaeo oil zone and water zone.

| Well Name | Current/Palaeo Oil Zone | | Water Zone | |
|---|---|---|---|---|
| | QGF Index | QGF Ratio | QGF Index | QGF Ratio |
| Jabiru-1A | 105 | 4.2 | 3.3 | 1.0 |
| Skua-3 | 64 | 4.4 | 2.9 | 1.3 |
| Carollina-1 | 17 | 3.0 | 3.8 | 1.2 |
| Saladin-1 | 7.0 | 1.6 | 3.5 | 1.1 |
| Saffron-1 | 7.5 | 1.6 | 1.7 | 0.8 |
| Swift-1 | 7.0 | 2.0 | | |
| Challis-1 | 7.6 | 2.3 | 3.6 | 1.2 |
| Beach sand | | | 2.3 | 1.0 |

QGF Thresholds for Separating Water Zone Samples from Palaeo Oil Zone Samples

In the region being investigated, measurement of 150 samples from seven wells and one modern beach sand indicated the thresholds for separating water zone samples from oil zone, and palaeo oil zone samples had a QGF Index of 4 and a QGF ratio of 1.5 (Table 3, FIG. 3).

Baseline QGF Index and Ratio values were determined by measuring samples from known water-saturated reservoirs. A thoroughly cleaned sand sample from a modern beach deposit was used to measure the instrument response to sedimentary grains with minimal adsorbed hydrocarbons and no observed oil inclusions. Samples selected to determine the baseline in a reservoir were analysed using the GOI technique to verify that they had never been in contact with oil. These samples were cleaned using the procedure described in Table 1 to remove weakly adsorbed hydrocarbons.

The modern beach sand had a QGF Index of 2.3 and a QGF Ratio of 1.0 (Table 3). Water zone samples from oil wells had average QGF Index of 1.7 to 3.8, and average QGF Ratios of 0.8 to 1.3. Current/palaeo oil zone samples had average QGF Index of 7 to 105, and average QGF Ratios of 1.6 to 4.4. In the region being investigated the empirical thresholds for palaeo oil and oil zones were a QGF Index of 4 and a QGF Ratio of 1.5 (FIG. 3).

Examples of QGF Applied to Evaluation of Palaeo Oil Saturation in Oil Wells

The Quantitative Grain Fluorescence (QGF) method was applied to seven exploration and production wells in three different basins in the NW Shelf, Australia (Table 3). These wells contained oil producing zones, palaeo oil zones and water zones identified from field tests (RFT), geophysical log analysis, laboratory fluid saturation tests and other oil saturation indicators such as petrographic examination under UV light (GOI).

QGF Profiles for Current Oil Zone, Palaeo Oil Zones and Water Zones

FIG. 4 shows QGF Index profile for a production well from the Vulcan Sub-basin. A gamma ray log (GR) was used as a reservoir quality reference. The oil-producing interval above 1655 m had QGF Index of 17 to 250 and peaks in the QGF spectrum. Elevated QGF Index values of 8 to 210 and peaks in the QGF spectra occurred in the interval 1655 m to 1709 m, which was below the oil zone. This interval was interpreted as a palaeo oil zone.

Below 1709 m the QGF Indices were 2 to 4.5 and the QGF spectra were relatively flat, which was in a range similar to the modern beach sand sample. These data were consistent with this depth interval not having been exposed to high oil saturation and a palaeo oil water contact occurring between the 1709 m and 1715 m samples.

In the region investigated QGF data were obtained for 150 samples from seven oil producing wells, four of which contained palaeo oil zones defined by GOI measurements, and six of which contained a known water zone. These data, presented in FIG. 5, confirmed the baseline QGF data for water zone samples and the thresholds of QGF Index=4 and QGF ratio=1.5 for current/palaeo oil zones.

The field test data indicated that the spectral shape and profiles of QGF Index and QGF Ratio could be used to differentiate water zones from oil producing zones and palaeo oil zones. On the basis of 150 samples from seven wells in three sedimentary basins in the NW Shelf, Australia, the thresholds for QGF Index and QGF Ratio were empirically defined at 4 and 1.5, respectively for the region investigated.

QGF Conclusions

Measurement of Quantitative Grain Fluorescence (QGF) enabled the detection of oil zones and palaeo oil zones. Fluorescent light was measured as emitted from hydrocarbon compounds that were strongly adsorbed on component grains of reservoir rock and sealed in any fluid inclusions, when excited by ultraviolet (UV) light, after the rock had been subjected to stringent cleaning. Oil zones and palaeo oil zones were identified on a depth log of QGF data within reservoirs as zones with higher QGF Index values that were elevated above baseline and with observed spectral peaks in the QGF spectra. Rocks that had always been water saturated had baseline values of QGF Index less than 4, and QGF Ratio less than 1.5 and relatively flat QGF spectra.

Thresholds were used to differentiate water zone samples from current palaeo oil zone samples. Interpretation of the UV fluorescence intensity of surface adsorbed hydrocarbons and oil inclusions in spatially related samples from a well bore was made by comparison with an empirically derived QGF Index, QGF ratio, and spectral features.

Analyses of 150 samples from seven exploration and oil production wells and a modern beach sample indicated that, in the region investigated, empirical thresholds for current oil/palaeo oil zones and water zones had a QGF Index in excess of 4 and a QGF ratio in excess of 1.5.

Correlation with field test data, geophysical log analysis, laboratory fluid saturation tests and other oil saturation indicators such as GOI data indicated that the QGF method was able to effectively differentiate current and palaeo oil zones from water zones, using empirically derived threshold values.

Example 2

QGF-E (Quantitative Grain Fluorescence-Extract) was developed to detect zones currently containing oil by making measurements on samples of core and cuttings from oil wells. In favourable circumstances (with good reservoir quality and high oil saturation) the oil was producible. The QGF-E technique was a variant of the QGF (Quantitative Grain Fluorescence) technique to detect palaeo oil zones.

The QGF-E procedure involved measuring by fluorescence spectrophotometer the fluorescence spectrum of dissolved hydrocarbons in dichloromethane extracted from sedimentary grains in samples of core or cuttings after they had been cleaned by a predetermined procedure (described in more detail below). The cleaning steps were water wash, dichloromethane wash, hydrogen peroxide digestion and hydrochloric acid digestion, after which the sample was extracted by dichloromethane and the fluorescence spectrum of dissolved hydrocarbons was measured. The cleaning of the sample prior to solvent extraction was observed to remove liquid and soluble hydrocarbons, leaving residual hydrocarbons with an affinity for mineral surfaces, such as high molecular weight aromatic and polar hydrocarbons, and ashphaltene.

QGF and QGF-E were observed to differ from other techniques for detecting oil in rocks by solvent extraction in that the measurement was not of the whole oil (solvent extraction on sample as received or after removal of water) but on hydrocarbons that remained on the sedimentary grains after the QGF/QGF-E cleaning procedure. In tests conducted on current oil reservoirs QGF-E was observed to be higher in the oil zone than in the underlying water zone. QGF-E was also low in palaeo-oil zones.

TABLE 4

Comparison of response of GOI, QGF and QGF-E in oil zone, palaeo-oil zone and water zone.

|  | Oil Zone | Palaeo-oil Zone | Water Zone |
| --- | --- | --- | --- |
| GOI | high values | high values | low values |
| QGF | high values | high values | low values |
| QGF-E | high values | low values | low values |

QGF-E Procedure

Separation of Single Rock Grains

Core and cuttings samples were disaggregated into their component framework grains by gentle agitation. The grains were either dry or wet-sieved to select grain sizes typically in the >63 μm and <1 mm size fraction, which was found to give satisfactory results.

If a high proportion of shale or coal fragments diluted the quartz and feldspar grains then a grain concentrate was made by techniques such as magnetic separation (Franz Isodynamic Separator).

Cleaning of Grains

The QGF-E cleaning procedure comprised rinsing the grains with water for 10 minutes in an ultrasound bath to separate particles and remove liquid oil loosely adhering at the surface. Samples were oven dried at 60° C. and washed with dichloromethane (DCM) in an ultrasound bath for 10 minutes to remove soluble hydrocarbons. The sample was digested in 10% $H_2O_2$ at room temperature for 1 hour with periodic agitation to degrade and remove reactive organic compounds. The grains were then digested in 3.6% hydrochloric acid (HCl) for 20 minutes with periodic agitation to remove carbonate minerals and iron oxides and hydroxides.

In accordance with the QGF-E procedure, the remaining grains, comprising predominantly quartz and feldspar, were washed a second time with dichloromethane (Table 5). This second dichloromethane liquid was then recovered for spectral measurements.

The concentration of hydrogen peroxide was noted to be important, and use of concentrations over 10% resulted in diminished fluorescence intensity. No polar solvents were used.

TABLE 5

Laboratory procedure to clean quartz grains for QGF-E analysis.

| | |
| --- | --- |
| Disaggregation | Sample core or cuttings Crushed to single grains, wet sieved to obtain grains with a 1000 to 63 μm size distribution |
| Mineral separation | Magnetic separation of quartz and feldspar grains if required |
| Water | 10 minute ultrasound bath |
| DCM (Dichloromethane) | 10 minute ultrasound bath |
| $H_2O_2$ (10%) | 1 hour digestion at room temperature |
| HCl (3.6%) | 20 minute digestion |
| DCM (Dichloromethane)* | 10 minute ultrasound bath |

*This second dichloromethane liquid was recovered and its fluorescence spectrum measured.

Instrument Set-Up and Measurement Procedure

A Varian Cary Eclipse fluorescence spectrophotometer was used to carry out the QGF-E measurement. The instrument had a beam splitter to monitor and correct for variations in excitation intensity. Fluorescence intensity was measured as scaled counts from a photomultiplier detector.

An excitation wavelength of 260 nm was found to give appropriate fluorescence intensity for the analysis. This wavelength was selected to excite fluorescence in a wide range of compounds and to produce maximum fluorescence intensity. The fluorescence spectrum was measured from 300 to 600 nm.

Analysis of Liquid Samples

For UV transparency, liquid samples were analyzed in a quartz cuvette. Samples containing dispersed particles were observed to have a negative effect on fluorescence spectra. The main effect was to induce spikes in the fluorescence spectra, usually about twice to five times the nominal intensity at a specific wavelength. It was noted that centrifuging or leaving a turbid solution to settle, over a period of minutes or hours, reduced or eliminated this problem.

Before conducting a fluorescence measurement on a sample, a measurement on a solvent blank was performed. Using a new pipette for each sample, approx. 4 mL of the sample was transferred to the cuvette, which was placed in the holder within the Cary-Eclipse instrument.

Instrument Settings 260 nm Excitation wavelength
300 nm to 600 nm Emission wavelength
5 nm Excitation slit, 10 nm Emission slit
Medium scan rate
Excitation Filter: 250–395 nm
Emission Filter 295–1100 nm Fluorescence Spectra of Dissolved Hydrocarbon Extracts Four fractions of natural crude oil containing aromatic and polar compounds obtained by liquid phase chromatography displayed maxima in fluorescence emission in the 350–450 wavelength interval (FIG. 6). The coincidence of fluorescence peaks for these compounds with the maximum in the QGF-E spectrum suggested the QGF-E response was in part from relatively high molecular weight aromatic and polar compounds.

Display of QGF-E data

QGF-E data were interpreted by observing the spectra of the solvent extract. In a water zone, including a palaeo-oil zone, spectra samples were relatively flat. In oil zone samples there was an observed spectral peak at about 375 nm due to the presence of dissolved hydrocarbons.

Plotting the QGF-E intensities for samples within the depth intervals of interest made a graph of QGF-E versus depth. QGF-E was the intensity at the wavelength of maximum fluorescence. The QGF-E intensities were plotted as depth profiles beside one or more geophysical logs (eg. gamma ray log, density or neutron porosity logs, resistivity log). These logs served as a correlation tool, a reservoir quality reference, and to indicate the depth interval of oil saturated rock (see FIG. 7 below).

Jabiru-1A

At Jabiru 1A QGF-E intensities (maximum fluorescence intensity between 300 and 600 nm) in the oil zone had values from 80 to 260 photometer counts. Below the oil water contact QGF intensity was relatively low with values less than 25 photometer counts. QGF-E intensities were less than 20 counts in the water zone between 1715 and 1733 mRT.

QGF Index measurements were also presented in FIG. 7 and these showed elevated QGF Index values both in the current oil zone and palaeo-oil zone. QGF intensities in the water zone below the palaeo-oil zone were low.

QGF-E data was also able to be interpreted by observing the shape of fluorescence spectra (FIG. 8). In the water zone and palaeo-oil zone the QGF-E spectra were flat. In the oil zone the spectra had an observed peak. At Jabiru this peak was near 375 nm.

Corallina-1

At the Corallina-1 well there was a current oil zone with an oil water contact at 3242 mRT depth below which there was a palaeo-oil zone identified by measurements of fluorescence at the well site, GOI and QGF.

In the current oil zone above 3242 mRT the QGF-E measurements were 25 to 60 photometer counts. In the palaeo-oil zone QGF-E measurements were 10 to 30 photometer counts.

QGF-E Conclusions

QGF-E detected current oil zones by observing higher values of fluorescence intensity and peaks in the fluorescence spectra compared with the underlying water zone. QGF-E values in palaeo-oil zones were also low.

QGF-E measured the fluorescence spectrum of a dichloromethane extract of hydrocarbons of disaggregated rock grains after a prescribed wash with water, dichloromethane, digestion in hydrogen peroxide and hydrochloric acid.

This differed from the GOI and QGF techniques, which detected rocks that have or have had high oil saturations by observing higher values of GOI or QGF in current oil zones and palaeo-oil zones than in rocks that have never had high oil saturation (water zone).

QGF-E differed from other techniques involving solvent extraction which involved analysis of the whole oil in a sample obtained by extraction of sample as received or after removal of water by centrifuging or drying.

Whilst the invention has been described with reference to a number of preferred embodiments, it should be appreciated that the invention can be embodied in many other forms.

The invention claimed is:

1. A method for determining whether a rock that is capable of functioning as an oil reservoir has had or presently contains oil, including the steps of:
   (i) cleaning a sample of the rock in a manner such that at least some of any adsorbed oil on the rock will remain and any oil in inclusions within the rock remain intact;
   (ii) irradiating the cleaned sample with fluorescence inducing electromagnetic radiation and measuring emitted radiation from the sample; and
   (iii) comparing the emitted radiation measurement against a similarly determined measurement from a rock sample of a known oil reservoir, to determine whether or not the rock has had or presently contains oil.

2. A method as claimed in claim 1 wherein the rock is granular and is disaggregated into single grains prior to cleaning step (i).

3. A method as claimed in claim 1 wherein step (i) involved cleaning the sample in a manner that removes non-adsorbed liquid oil and contaminants.

4. A method as claimed in claim 3 wherein the contaminants include additives in drilling mud.

5. A method as claimed in claim 1 wherein, when the rock is granular, the sample is disaggregated into single grains and step (i) then includes the steps of:
   (a) sieving the sample; and
   (b) subjecting the sieved sample to ultrasound and solvent washing/digestion.

6. A method as claimed in claim 5 wherein step (b) solvent washing/digestion includes washing the grains with water and dichloromethane, and digestion with hydrogen peroxide solution and acid solution.

7. A method as claimed in claim 6 wherein, after digestion, a final step of solvent washing is employed in step (i) of claim 1.

8. A method as claimed in claim 7 wherein the solvent used for solvent washing is dichloromethane.

9. A method for determining whether a rock that is capable of functioning as an oil reservoir has had or presently contains oil, including the steps of:
   (i) step-wise cleaning a sample of the rock comprising the steps of washing the sample in a first step and digesting the sample in a second step with the first and second steps removing other than adsorbed oil on the rock, with a final cleaning step including contacting the sample with a solvent into which some adsorbed oil may be extracted; and either:
   (iia) irradiating the cleaned rock sample with fluorescence inducing electromagnetic radiation and measuring emitted radiation from the sample; or
   (iib) analysing oil extracted into the solvent of the final cleaning step; and
   (iii) in the case of step (iia) comparing the emitted radiation measurement against a similarly determined measurement from a rock sample of a known oil reservoir; or in the case of step (iib) comparing the analysed oil against a similarly derived and analysed oil from a rock sample of a known oil reservoir; to determine whether or not the rock has had or presently contains oil.

10. A method as claimed in claim 9 wherein the step (iib) oil analysis involves irradiating the solvent with fluorescence inducing electromagnetic radiation and measuring emitted radiation from the solvent.

11. A method as claimed in claim 9 wherein the sample of step (iia) or the solvent of step (iib) is irradiated with ultra-violet (UV) radiation and a characterizing fluorescence spectra of the adsorbed oil of step (iia) or the solvent extracted oil of step (iib) is measured.

12. A method as claimed in claim 11 wherein UV radiation includes wavelengths of about 260 nm, and the characterising fluorescence spectra is measured in the range of 300 to 600 nm using a fluorescence spectrophotometer.

13. A method as claimed in claim 12 wherein a mean intensity of emitted radiation is computed for wavelengths of 375 to 475 nm and is normalised to an intensity at 300 nm, and is then compared against that of a known rock sample.

14. A method as claimed in claim 9 wherein, when the rock is granular, the sample is disaggregated into single grains and step (i) then includes the steps of:

(a) sieving the sample;

(b) subjecting the sieved sample to ultrasound and solvent washing/digestion; and (c) after digestion, employing a final step of solvent washing.

15. A method as claimed in claim 14 wherein the solvent from the final washing step (c) is discarded in the case of step (iia) of claim 9, or is used as the solvent for step (iib) of claim 9.

* * * * *